(12) United States Patent
Doan et al.

(10) Patent No.: US 12,564,717 B2
(45) Date of Patent: Mar. 3, 2026

(54) PARESTHESIA-FREE SPINAL CORD STIMULATION OCCURRING AT LOWER FREQUENCIES INVOLVING PERCEPTION THRESHOLD DETERMINATIONS

(71) Applicant: Boston Scientific Neuromodulation Corporation, Valencia, CA (US)

(72) Inventors: Que T. Doan, West Hills, CA (US); Luca Antonello Annecchino, London (GB)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1223 days.

(21) Appl. No.: 17/347,348

(22) Filed: Jun. 14, 2021

(65) Prior Publication Data

US 2021/0299448 A1     Sep. 30, 2021

Related U.S. Application Data

(63) Continuation-in-part of application No. 16/806,065, filed on Mar. 2, 2020, now Pat. No. 11,338,141, (Continued)

(51) Int. Cl.
*A61N 1/36* (2006.01)
*A61N 1/05* (2006.01)
(Continued)

(52) U.S. Cl.
CPC ....... *A61N 1/36062* (2017.08); *A61N 1/0551* (2013.01); *A61N 1/36021* (2013.01);
(Continued)

(58) Field of Classification Search
CPC .... A61N 1/06; A61N 1/37247; A61N 1/0551; A61N 1/36062
See application file for complete search history.

(56) References Cited

U.S. PATENT DOCUMENTS 6,181,969 B1     1/2001  Gord
6,516,227 B1     2/2003  Meadows et al.
(Continued)

FOREIGN PATENT DOCUMENTS

CN     202933390          5/2013
CN     102448539 B     10/2014
(Continued)

OTHER PUBLICATIONS

International Search Report and Written Opinion regarding corresponding PCT Application No. PCT/US2021/037272, mailed Mar. 1, 2022.
(Continued)

*Primary Examiner* — Joseph M Dietrich
(74) *Attorney, Agent, or Firm* — Lewis & Reese, PLLC

(57) ABSTRACT

Methods and systems for testing and treating spinal cord stimulation (SCS) patients are disclosed. Patients are eventually treated with sub-perception (paresthesia free) therapy. However, supra-perception stimulation is used during "sweet spot searching" during which a stimulation location in an electrode array is determined. Preferably, the supra-perception stimulation comprises a bipole formed using actively-driven symmetric biphasic waveforms at active ones of the electrodes in the array. After determining the location, a perception threshold for the bipole at the location is determined and stored, and an amplitude of the stimulation is reduced below the perception threshold to provide a sub-perception stimulation bipole. The determined perception threshold may be transmitted to the patient's remote controller, where it is used to limit amplitude adjustments to the sub-perception bipole by the patient.

18 Claims, 9 Drawing Sheets

Related U.S. Application Data which is a continuation of application No. 16/100,904, filed on Aug. 10, 2018, now Pat. No. 10,576,282.

(60) Provisional application No. 62/693,543, filed on Jul. 3, 2018, provisional application No. 62/544,656, filed on Aug. 11, 2017.

(51) Int. Cl.
*A61N 1/372*        (2006.01)
*A61N 1/06*         (2006.01)

(52) U.S. Cl.
CPC ..... *A61N 1/36071* (2013.01); *A61N 1/36185* (2013.01); *A61N 1/37247* (2013.01); *A61N 1/06* (2013.01); *A61N 1/36132* (2013.01); *A61N 1/37235* (2013.01); *A61N 1/37252* (2013.01)

(56) References Cited

U.S. PATENT DOCUMENTS

| | | | |
|---|---|---|---|
| 7,603,177 B2 | 10/2009 | Sieracki et al. | |
| 8,180,451 B2 | 5/2012 | Hickman et al. | |
| 8,359,102 B2 | 1/2013 | Alataris et al. | |
| 8,515,546 B2 | 8/2013 | Goddard et al. | |
| 8,606,360 B2 | 12/2013 | Butson et al. | |
| 8,606,362 B2 | 12/2013 | He et al. | |
| 8,620,436 B2 | 12/2013 | Parramon et al. | |
| 8,712,533 B2 | 4/2014 | Alataris et al. | |
| 8,792,988 B2 | 7/2014 | Alataris et al. | |
| 9,259,574 B2 | 2/2016 | Aghassian et al. | |
| 9,327,125 B2 | 5/2016 | Alataris et al. | |
| 9,333,357 B2 | 5/2016 | Alataris et al. | |
| 9,446,243 B2 | 9/2016 | Marnfeldt et al. | |
| 9,480,842 B2 | 11/2016 | Alataris et al. | |
| 9,789,252 B2 | 10/2017 | Gerber et al. | |
| 9,792,412 B2 | 10/2017 | Moffitt et al. | |
| 11,285,323 B2 * | 3/2022 | Doan ................... | A61N 1/0551 |
| 2002/0193833 A1 | 12/2002 | Dimmer et al. | |
| 2009/0204175 A1 | 8/2009 | Zanella et al. | |
| 2010/0023090 A1 | 1/2010 | Jaax et al. | |
| 2010/0274312 A1 | 10/2010 | Alataris et al. | |
| 2010/0305675 A1 | 12/2010 | Laske et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2013/0053923 A1 | 2/2013 | Jaax et al. | |
| 2013/0116752 A1 | 5/2013 | Parker et al. | |
| 2013/0268026 A1 | 10/2013 | Rao et al. | |
| 2014/0277251 A1 | 9/2014 | Gerber et al. | |
| 2014/0277267 A1 | 9/2014 | Vansickle | |
| 2014/0364919 A1 | 12/2014 | Doan | |
| 2015/0080982 A1 | 3/2015 | Funderburk | |
| 2015/0231402 A1 | 8/2015 | Aghassian | |
| 2015/0335893 A1 | 11/2015 | Parker | |
| 2015/0360038 A1 | 12/2015 | Zottola et al. | |
| 2016/0082265 A1 | 3/2016 | Moffitt et al. | |
| 2016/0114166 A1 | 4/2016 | Kaula et al. | |
| 2016/0144183 A1 | 5/2016 | Marnfeldt | |
| 2016/0158551 A1 | 6/2016 | Kent et al. | |
| 2016/0317815 A1 | 11/2016 | Doan et al. | |
| 2016/0361543 A1 | 12/2016 | Kaula et al. | |
| 2016/0367822 A1 | 12/2016 | Parramon | |
| 2017/0050035 A1 | 2/2017 | Gupta et al. | |
| 2017/0056642 A1 | 3/2017 | Moffitt et al. | |
| 2017/0106197 A1 | 4/2017 | Wechter et al. | |
| 2017/0165490 A1 | 6/2017 | Wechter | |
| 2017/0173335 A1 | 6/2017 | Min et al. | |
| 2017/0189685 A1 | 7/2017 | Steinke et al. | |
| 2018/0043172 A1 | 2/2018 | Serrano Carmona | |
| 2018/0071513 A1 | 3/2018 | Weiss et al. | |
| 2018/0071520 A1 | 3/2018 | Weerakoon et al. | |
| 2018/0104493 A1 | 4/2018 | Doan et al. | |
| 2019/0009094 A1 | 1/2019 | Zhang et al. | |
| 2019/0046800 A1 | 2/2019 | Doan et al. | |
| 2019/0083796 A1 | 3/2019 | Weerakoon et al. | |
| 2019/0175915 A1 | 6/2019 | Brill et al. | |
| 2019/0209844 A1 | 7/2019 | Esteller et al. | |
| 2019/0290900 A1 | 9/2019 | Esteller et al. | |
| 2019/0366104 A1 | 12/2019 | Doan et al. | |
| 2020/0009367 A1 | 1/2020 | Huertas Fernandez et al. | |
| 2020/0009394 A1 | 1/2020 | Huertas Fernandez et al. | |
| 2020/0046980 A1 | 2/2020 | Moffitt et al. | |
| 2020/0147397 A1 | 5/2020 | Huertas Fernandez et al. | |

FOREIGN PATENT DOCUMENTS

| | | |
|---|---|---|
| EP | 2923727 | 9/2015 |
| JP | 2013-126486 | 6/2013 |
| WO | 2014/130865 | 8/2014 |
| WO | 2015/066303 | 5/2015 |
| WO | 2016/176425 A1 | 11/2016 |
| WO | 2017/106539 | 6/2017 |
| WO | 2020/251899 | 12/2020 |
| WO | 2021/003290 A1 | 1/2021 |
| WO | 2021/141652 A1 | 7/2021 |
| WO | 2021/178105 A1 | 9/2021 |

OTHER PUBLICATIONS

L. Kapural et al., "Novel 10-kHz High-frequency Therapy (HF10 Therapy) Is Superior to Traditional Low-frequency Spinal Cord Stimulation for the Treatment of Chronic Back and Leg Pain," Anesthesiology 2015; 123:851-60 (Oct. 2015).

S. Thomson et al., "The PROCO Randomised Controlled Trial: Effects of Pulse Rate on Clinical Outcomes in Kilohertz Frequency Spinal Cord Stimulation—A Multicentre, Double-blind, Crossover Study," presented at the International Neuromodulation Society (INS) Meeting on May 31, 2017.

E.C. Celik et al., "The effect of low-frequency TENS in the treatment of neuropathic pain in patients with spinal cord injury," Spinal Cord 51:34-337 (2013).

Y. Maeda et al., "Low frequencies, but not high frequencies of bi-polar spinal cord stimulation reduce cutaneous and muscle hyperalgesia induced by nerve injury," Pain 138:143-152 (2008).

S. Thomson et al., "Neural Dosing and Energy Requirements in Kilohertz Frequency Spinal Cord Stimulation (SCS)," poster presented at the International Neuromodulation Society (INS) Meeting on May 31, 2017.

S. Paz et al., "Improved Efficacy of SCS Implants Using Multiple Waveforms and Field Shape Options," poster presented at the International Neuromodulation Society (INS) Meeting on May 31, 2017.

S. Paz et al., "Evaluation of Customized Field Shape for Subperception SCS in a Case Series of Chronic Pain Patients," poster presented at the North American Neuromodulation Society (NANS) Meeting on Jan. 11-14, 2018.

S.J. Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21(1), pp. 67-76 (2018) (published on-line Dec. 8, 2017).

J.M. North et al., "Clinical Outcomes of 1 kHz Subperception Spinal Cord Stimulation in Implanted Patients With Failed Paresthesia-Based Stimulation: Results of a Prospective Randomized Controlled Trial," Neuromodulation: Technology at the Neural Interface, vol. 19(7), pp. 731-737 (2016).

Yearwood, Thomas, et al., Handout titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.

Yearwood, Thomas, et al., Poster titled "A Prospective Comparison of Spinal Cord Stimulation (SCS) Using Dorsal Column Stimulation (DCS), Intraspinal Nerve Root Stimulation (INRS), and Vary-

(56) References Cited

OTHER PUBLICATIONS ing Pulse Width in the Treatment of Chronic Low Back Pain," Congress of Neurological Surgeons 56th Annual Meeting, Oct. 7-12, 2006, 7 pages.

Yearwood, Thomas, "Neuropathic Extremity Paid and Spinal Cord Stimulation," Pain Medicine, vol. 7, No. S1, 2006, 6 pages.

A. Al-Kaisy et al., "Prospective, Randomized, Sham-Control, Double Blind, Crossover Trial of Subthreshold Spinal Cord Stimulation at Various Kilohertz Frequencies in Subjects Suffering From Failed Back Surgery Syndrome (SCS Frequency Study)," Neuromodulation, vol. 21(5), pp. 457-465 (2018).

M. De Jaeger M et al., "High-Density in Spinal Cord Stimulation: Virtual Expert Registry (DISCOVER): Study Protocol for a Prospective Observational Trial," Anesth. Pain Med., vol. 7(3) (2017).

T.E. Hamm-Faber et al., "High-Dose Spinal Cord Stimulation for Treatment of Chronic Low Back Pain and Leg Pain in Patients With FBSS, 12-Month Results: a Prospective Pilot Study," Neuromodulation, E-pub ahead of print, DOI:10.1111/ner.12940 (2019).

L. Kapural et al., "Novel 10-kHz High-frequency Therapy (HF10 Therapy) Is Superior to Traditional Low-frequency Spinal Cord Stimulation for the Treatment of Chronic Back and Leg Pain: The SENZA-RCT Randomized Controlled Trial," Anesthesiology, vol. 123(4), pp. 851-860 (2015).

J.P. Miller et al., "Parameters of Spinal Cord Stimulation and Their Role in Electrical Charge Delivery: a Review," Neuromodulation, vol. 19(4), pp. 373-384 (2016).

Z. Chen et al., "The Impact of Electrical Charge Delivery on Inhibition of Mechanical Hypersensitivity in Nerve-Injured Rats by Sub-Sensory Threshold Spinal Cord Stimulation," Neuromodulation, vol. 22(2), pp. 163-171 (2019).

F. Yang et al., "Modulation of Spinal Nociceptive Transmission by Sub-Sensory Threshold Spinal Cord Stimulation in Rats After Nerve Injury," Neuromodulation, E-pub ahead of print, DOI:10.1111/ner.12975 (2019).

S.L. Leong et al., "Potential Therapeutic Effect of Low Amplitude Burst Spinal Cord Stimulation on Pain," Neuromodulation, E-pub ahead of print, DOI:10.1111/ner.13090 (2019).

T. Deer et al., "Success Using Neuromodulation With Burst (Sunburst) Study: Results From a Prospective, Randomized Controlled Trial Using a Novel Burst Waveform," Neuromodulation, vol. 21(1), pp. 56-66 (2018).

F. Wille et al., "Altering Conventional to High Density Spinal Cord Stimulation: an Energy Dose-Response Relationship in Neuropathic Pain Therapy," Neuromodulation, vol. 20(1), pp. 71-80 (2017).

J. Vesper et al., "Burst SCS Microdosing Is as Efficacious as Standard Burst SCS in Treating Chronic Back and Leg Pain: Results From a Randomized Controlled Trial," Neuromodulation, vol. 22(2), pp. 190-193 (2019).

E. Tavel et al., "Lower Amplitudes for Burst SCS Programming Associated with Improved Outcomes: SUNBURST Sub-Analysis," International Neuromodulation Society (INS) annual meeting, poster, (2017).

* cited by examiner

PARESTHESIA-FREE SPINAL CORD STIMULATION OCCURRING AT LOWER FREQUENCIES INVOLVING PERCEPTION THRESHOLD DETERMINATIONS

CROSS-REFERENCE TO RELATED APPLICATIONS

This application is a continuation-in-part of U.S. patent application Ser. No. 16/806,065, filed Mar. 2, 2020, which is a continuation of U.S. patent application Ser. No. 16/100, 904, filed Aug. 10, 2018, which is a non-provisional application of U.S. Provisional Patent Application Ser. Nos. 62/544,656, filed Aug. 11, 2017, and 62/693,543, filed Jul. 3, 2018. Priority is claimed to these applications, and they are incorporated herein by reference in their entireties.

FIELD OF THE INVENTION

This application relates to Implantable Medical Devices (IMDs), generally, Spinal Cord Stimulators, more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

In the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal electrodes 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

IPG 10 can include an antenna 26a allowing it to communicate bi-directionally with a number of external devices, as shown in FIG. 4. The antenna 26a as depicted in FIG. 1 is shown as a conductive coil within the case 12, although the coil antenna 26a can also appear in the header 23. When antenna 26a is configured as a coil, communication with external devices preferably occurs using near-field magnetic induction. IPG may also include a Radio-Frequency (RF) antenna 26b. In FIG. 1, RF antenna 26b is shown within the header 23, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

In the example of FIG. 2, electrode E5 has been selected as an anode, and thus provides pulses which source a positive current of amplitude +A to the tissue. Electrode E4 has been selected as a cathode, and thus provides pulses which sink a corresponding negative current of amplitude-A from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time (e.g., tripole stimulation, quadripole stimulation, etc.).

The pulses as shown in FIG. 2 are biphasic, comprising a first phase 30a, followed quickly thereafter by a second phase 30b of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30a and discharged (be recovered) during the second phase 30b. In the example shown, the first and second phases 30a and 30b have the same duration and amplitude (although opposite polarities), which ensures the same amount of charge during both phases. However, the second phase 30b may also be charged balance with the first phase 30a if the integral of the amplitude and durations of the two phases are equal in magnitude, as is well known. The width of each pulse, PW, is defined here as the duration of first pulse phase 30a, although pulse width could also refer to the total duration of the first and second pulse phases 30a and 30b as well. Note that an interphase period (IP) during which no stimulation is provided may be provided between the two phases 30*a* and 30*b*.

IPG 10 includes stimulation circuitry 28 that can be programmed to produce the stimulation pulses at the electrodes as defined by the stimulation program. Stimulation circuitry 28 can for example comprise the circuitry described in U.S. Patent Application Publications 2018/0071513 and 2018/0071520, or in U.S. Pat. Nos. 8,606,362 and 8,620,436. These references are incorporated herein by reference.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial leads 15' are implanted in the patient's tissue 32 at a target location 34, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42*a*, and/or a far-field RF antenna 42*b*, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a patient, hand-held external controller 45, and a clinician programmer (CP) 50. Both of devices 45 and 50 can be used to send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47*a* capable of wirelessly communicating with the coil antenna 26*a* or 42*a* in the IPG 10 or ETS 40. The external controller 45 can also have a far-field RF antenna 47*b* capable of wirelessly communicating with the RF antenna 26*b* or 42*b* in the IPG 10 or ETS 40.

The external controller 45 can also have control circuitry 48 such as a microprocessor, microcomputer, an FPGA, other digital logic structures, etc., which is capable of executing instructions an electronic device. Control circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 26*a* or 42*a*, wand 54 can likewise include a coil antenna 56*a* to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

If the IPG 10 or ETS 40 includes an RF antenna 26*b* or 42*b*, the wand 54, the computing device 51, or both, can likewise include an RF antenna 56*b* to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

A portion of the GUI 64 is shown in one example in FIG. 5. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected as the only anode to source current, and this electrode receives X=100% of the specified anodic current, +A. Likewise, electrode E4 has been selected as the only cathode to sink current, and this electrode receives X=100% of that cathodic current, −A.

The GUI 64 as shown specifies only a pulse width PW of the first pulse phase 30a. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30a and 30b (e.g., each having a duration of PW, and with opposite polarities +A and −A). An advanced menu 88 can also be used (among other things) to define the relative durations and amplitudes of the pulse phases 30a and 30b, and to allow for other more advance modifications, such as setting of a duty cycle (on/off time) for the stimulation pulses, and a ramp-up time over which stimulation reaches its programmed amplitude (A), etc. A mode menu 90 allows the clinician to choose different modes for determining stimulation parameters. For example, as described in the '038 Publication, mode menu 90 can be used to enable electronic trolling, which comprises an automated programming mode that performs current steering along the electrode array by moving the cathode in a bipolar fashion.

While GUI 64 is shown as operating in the clinician programmer 50, the user interface of the external controller 45 may provide similar functionality.

SUMMARY

A method is disclosed for programming a stimulator having a plurality of electrodes comprising an array. The method may comprise: (a) using a first external device to provide a stimulation field to the stimulator, wherein the stimulation field comprises a pole configuration formed in the electrode array; (b) using the first external device to move the pole configuration in the electrode array to a location that best treats a symptom of the patient; (c) determining using the first external device a threshold of the pole configuration at the location by varying an amplitude of the stimulation field; (d) adjusting the amplitude using the first external device to below the perception threshold to produce sub-perception stimulation at the location; and (e) using the first external device to program a second external device usable by the patient with the determined perception threshold, wherein the second external device is useable by the patient to adjust an amplitude of the sub-perception stimulation, wherein the perception threshold limits adjustment of the amplitude by the patient.

In one example, the first external device programs the second external device to a default amplitude of less than pth. In one example, the stimulator comprises a spinal cord stimulator. In one example, the stimulation field provides supra-perception stimulation. In one example, the threshold comprises a perception threshold. In one example, the pole configuration comprises a bipole comprising an anode pole and a cathode pole. In one example, when the bipole is at the location, the anode pole is formed at two or more electrodes, and wherein the cathode pole is formed at two or more different of the electrodes. In one example, the bipole comprises and anode pole and a cathode pole, wherein more than one electrode is active to form the anode pole, and wherein more than one electrode is active to form the cathode pole. In one example, the first external device is used to move the pole configuration linearly along a length of the electrode array. In one example, the pole configuration comprises actively-driven symmetric biphasic pulses at active ones of the electrodes. In one example, the pulses are formed at a frequency of 130 Hz or less. In one example, the pulses have a pulse width within a range from 50 to 500 microseconds. In one example, the pulses have a pulse width within a range from 160 to 260 microseconds. In one example, the method is initiated at the external device by receiving a mode selection at an interface of the external device. In one example, in step (d) the amplitude is adjusted to a programmed fraction of the perception threshold. In one example, in step (e) the amplitude adjustment at the second external device cannot exceed the perception threshold.

A first external device is disclosed to program a stimulator having a plurality of electrodes comprising an array, which may comprise: control circuitry configured to render a user interface, wherein the user interface enables a user to (a) provide a stimulation field to the stimulator, wherein the stimulation field comprises a pole configuration formed in the electrode array; (b) move the pole configuration in the electrode array to a location that best treats a symptom of the patient; (c) determine a threshold of the pole configuration at the location by varying an amplitude of the stimulation field; (d) adjust the amplitude to below the perception threshold to produce sub-perception stimulation at the location; and (e) program a second external device usable by the patient with the determined perception threshold, wherein the second external device is useable by the patient to adjust an amplitude of the sub-perception stimulation, wherein the perception threshold limits adjustment of the amplitude by the patient.

In one example, the control circuitry is configured to program the second external device to a default amplitude of less than pth. In one example, the stimulator comprises a spinal cord stimulator. In one example, the stimulation field provides supra-perception stimulation. In one example, the threshold comprises a perception threshold. In one example, the pole configuration comprises a bipole comprising an anode pole and a cathode pole. In one example, when the bipole is at the location, the anode pole is formed at two or more electrodes, and wherein the cathode pole is formed at two or more different of the electrodes. In one example, the bipole comprises and anode pole and a cathode pole, wherein more than one electrode is active to form the anode pole, and wherein more than one electrode is active to form the cathode pole. In one example, the pole configuration comprises actively-driven symmetric biphasic pulses at active ones of the electrodes. In one example, the pulses are formed at a frequency of 130 Hz or less. In one example, the pulses have a pulse width within a range from 50 to 500 microseconds. In one example, the pulses have a pulse width within a range from 160 to 260 microseconds. In one example, the user interface comprises a mode selection to enable the performance of steps (a)-(e). In one example, in step (d) the amplitude is adjusted to a programmed fraction of the perception threshold. In one example, in step (e) the amplitude adjustment at the second external device cannot exceed the perception threshold.

A non-transitory computer readable medium is disclosed containing instructions executable on a first external device configured to program a stimulator having a plurality of electrodes comprising an array, wherein the instruction when executed enable a user to: (a) provide a stimulation field to the stimulator, wherein the stimulation field comprises a pole configuration formed in the electrode array; (b) move the pole configuration in the electrode array to a location that best treats a symptom of the patient; (c) determine a threshold of the pole configuration at the location by varying an amplitude of the stimulation field; (d) adjust the amplitude to below the perception threshold to produce sub-perception stimulation at the location; and (e) program a second external device usable by the patient with the determined perception threshold, wherein the second external device is useable by the patient to adjust an amplitude of the sub-perception stimulation, wherein the perception threshold limits adjustment of the amplitude by the patient.

DETAILED DESCRIPTION

While Spinal Cord Stimulation (SCS) therapy can be an effective means of alleviating a patient's pain, such stimulation can also cause paresthesia. Paresthesia-sometimes referred to a "supra-perception" therapy—is a sensation such as tingling, prickling, heat, cold, etc. that can accompany SCS therapy. Generally, the effects of paresthesia are mild, or at least are not overly concerning to a patient. Moreover, paresthesia is generally a reasonable tradeoff for a patient whose chronic pain has now been brought under control by SCS therapy. Some patients even find paresthesia comfortable and soothing.

Nonetheless, at least for some patients, SCS therapy would ideally provide complete pain relief without paresthesia-what is often referred to as "sub-perception" or sub-threshold therapy that a patient cannot feel. Effective sub-perception therapy may provide pain relief without paresthesia by issuing stimulation pulses at higher frequencies. Unfortunately, such higher-frequency stimulation may require more power, which tends to drain the battery 14 of the IPG 10. See, e.g., U.S. Patent Application Publication 2016/0367822. If an IPG's battery 14 is a primary cell and not rechargeable, high-frequency stimulation means that the IPG 10 will need to be replaced more quickly. Alternatively, if an IPG battery 14 is rechargeable, the IPG 10 will need to be charged more frequently, or for longer periods of time. Either way, the patient is inconvenienced.

In an SCS application, it is desirable to determine a stimulation program that will be effective for each patient. A significant part of determining an effective stimulation program is to determine a "sweet spot" for stimulation in each patient, i.e., to select which electrodes should be active (E) and with what polarities (P) and relative amplitudes (X %) to recruit and thus treat a neural site at which pain originates in a patient. Selecting electrodes proximate to this neural site of pain can be difficult to determine, and experimentation is typically undertaken to select the best combination of electrodes to provide a patient's therapy.

As described in U.S. Patent Application Publication 2019/0366104, which is hereby expressly incorporated by reference, selecting electrodes for a given patient can be even more difficult when sub-perception therapy is used, because the patient does not feel the stimulation, and therefore it can be difficult for the patient to feel whether the stimulation is "covering" or masking his pain and therefore whether selected electrodes are effective. Further, sub-perception stimulation therapy may require a "wash in" period before it can become effective. A wash in period can take up to a day or more, and therefore sub-perception stimulation may not be immediately effective, making electrode selection more difficult.

Figure 6:
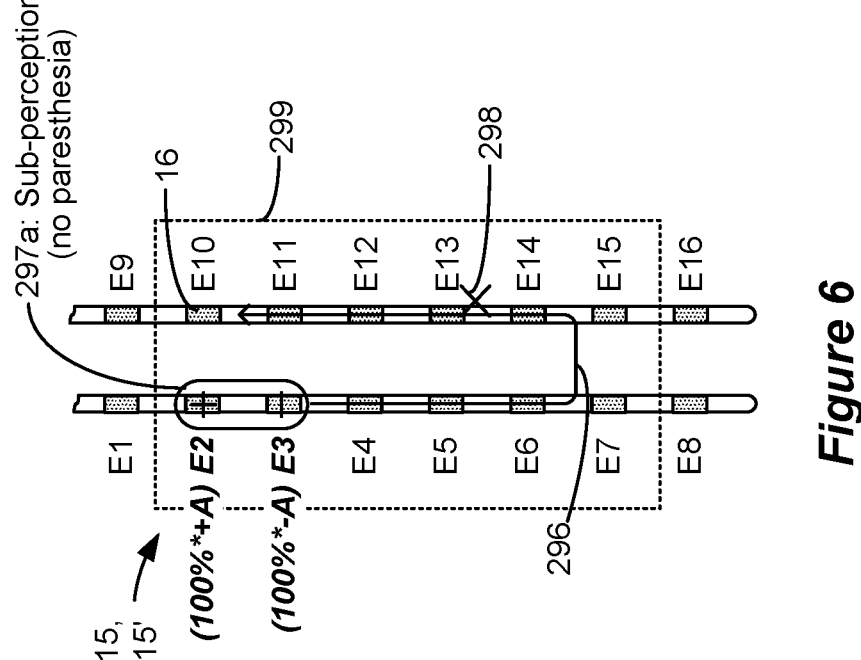
FIG. 6 shows sweet spot searching to determine effective electrodes for a patient using a movable sub-perception bipole.

FIG. 6 briefly explains the '104 Publication's technique for a sweet spot search, i.e., how electrodes can be selected that are proximate to a neural site of pain 298 in a patient, when sub-perception stimulation is used. The technique of FIG. 6 is particularly useful in a trial setting after a patient is first implanted with an electrode array, i.e., after receiving their IPG or ETS.

In the example shown, it is assumed that a pain site 298 is likely within a tissue region 299. Such region 299 may be deduced by a clinician based on the patient symptoms, e.g., by understanding which electrodes are proximate to certain vertebrae (not shown), such as within the T9-T10 interspace. In the example shown, region 299 is bounded by electrodes E2, E7, E15, and E10, meaning that electrodes outside of this region (e.g., E1, E8, E9, E16) are unlikely to have an effect on the patient's symptoms. Therefore, these electrodes may not be selected during the sweet spot search depicted in FIG. 6, as explained further below.

Figures 1, 2, 3:
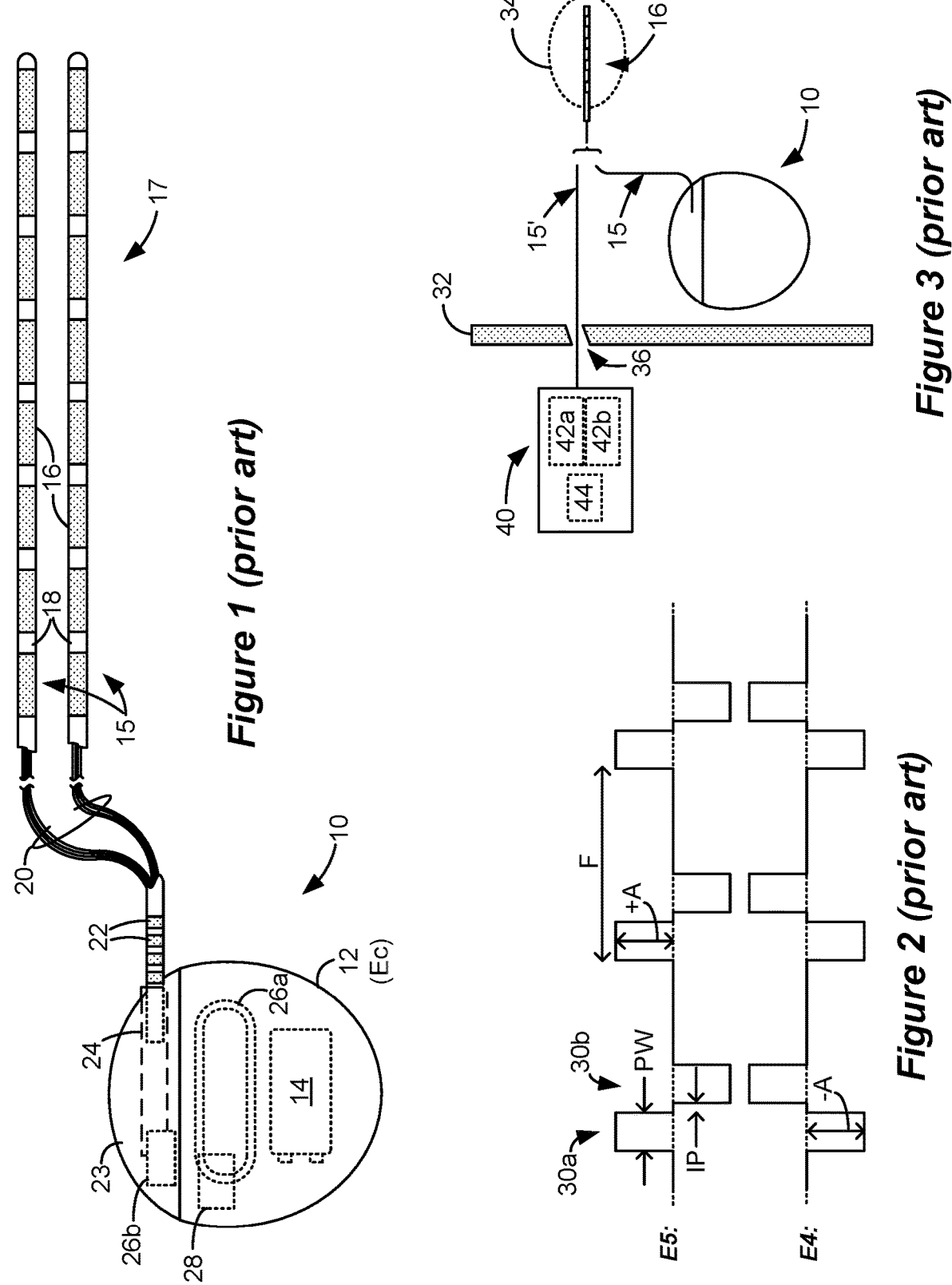
FIG. 1 shows an Implantable Pulse Generator (IPG) useable for Spinal Cord Stimulation (SCS), in accordance with the prior art.
FIG. 2 shows an example of stimulation pulses producible by the IPG, in accordance with the prior art.
FIG. 3 shows use of an External Trial Stimulator (ETS) useable to provide stimulation before implantation of an IPG, in accordance with the prior art.

In FIG. 6, a sub-perception bipole 297a is selected, in which one electrode (e.g., E2) is selected as an anode that will source a positive current (+A) to the patient's tissue, while another electrode (e.g., E3) is selected as a cathode that will sink a negative current (−A) from the tissue. This is similar to what was illustrated earlier with respect to FIG. 2, and biphasic stimulation pulses can be used employing active charge recovery. Because the bipole 297a provides sub-perception stimulation, the amplitude A used during the sweet spot search is titrated down until the patient no longer feels paresthesia. This sub-perception bipole 297a is provided to the patient for a duration, such as a few days, which allows the sub-perception bipole's potential effectiveness to "wash in," and allows the patient to provide feedback concerning how well the bipole 297a is helping their symptoms. Such patient feedback can comprise a pain scale ranking. For example, the patient can rank their pain on a scale from 1-10 using a Numerical Rating Scale (NRS) or the Visual Analogue Scale (VAS), with 1 denoting no or little pain and 10 denoting a worst pain imaginable. As discussed in the '104 Publication, such pain scale ranking can be entered into the patient's external controller 45.

After the bipole 297a is tested at this first location, a different combination of electrodes is chosen (anode electrode E3, cathode electrode E4), which moves the location of the bipole 297 in the patient's tissue. Again, the amplitude of the current A may need to be titrated to an appropriate sub-perception level. In the example shown, the bipole 297a is moved down one electrode lead, and up the other, as shown by path 296 in the hope of finding a combination of electrodes that covers the pain site 298. In the example of FIG. 6, given the pain site 298's proximity to electrodes E13 and E14, it might be expected that a bipole 297a at those electrodes will provide the best relief for the patient, as reflected by the patient's pain score rankings. The particular stimulation parameters chosen when forming bipole 297a can be selected at the GUI 64 of the clinician programmer 50 or other external device (such as a patient external controller 45) and wirelessly telemetered to the patient's IPG or ETS for execution. Note that the bipole 297a can be moved up, down, left, or right using directional arrows 99 provided in the GUI 64 of the CP 50. Alternatively, the bipole can be moved using a peripheral device connected to the CP 50, such as a mouse or joystick.

While the sweet spot search of FIG. 6 can be effective, it can also take a significantly long time when sub-perception stimulation is used. As noted, sub-perception stimulation is provided at each bipole 297 location for a number of days, and because a large number of bipole locations are chosen, the entire sweep spot search can take up to a month to complete.

The inventors have determined via testing of SCS patients that even if it is desired to eventually use sub-perception therapy for a patient going forward after the sweet spot search, it is beneficial to use supra-perception stimulation during the sweet spot search to select active electrodes for the patient. Use of supra-perception stimulation during the sweet spot search greatly accelerates determination of effective electrodes for the patient compared to the use of sub-perception stimulation, which requires a wash in period at each set of electrodes tested. After determining electrodes for use with the patient using supra-perception therapy, therapy may be titrated to sub-perception levels keeping the same electrodes determined for the patient during the sweet spot search. Because the selected electrodes are known to be recruiting the neural site of the patient's pain, the application of sub-perception therapy to those electrodes is more likely to have immediate effect, reducing or potentially eliminating the need to wash in the sub-perception therapy that follows. In short, effective sub-perception therapy can be achieved more quickly for the patient when supra-perception sweet spot searching is utilized. Preferably, supra-perception sweet spot searching occurs using symmetric biphasic pulses occurring at low frequencies-such as between 40 and 200 Hz in one example.

In accordance with one aspect of the disclosed technique, a patient will be provided sub-perception therapy. Sweet spot searching to determine electrodes that may be used during sub-perception therapy may precede such sub-perception therapy. In some aspects, when sub-perception therapy is used for the patient, sweet spot searching may use a bipole 297a that is sub-perception (FIG. 6), as just described. This may be relevant because the sub-perception sweet spot search may match the eventual sub-perception therapy the patient will receive.

Figure 7A:
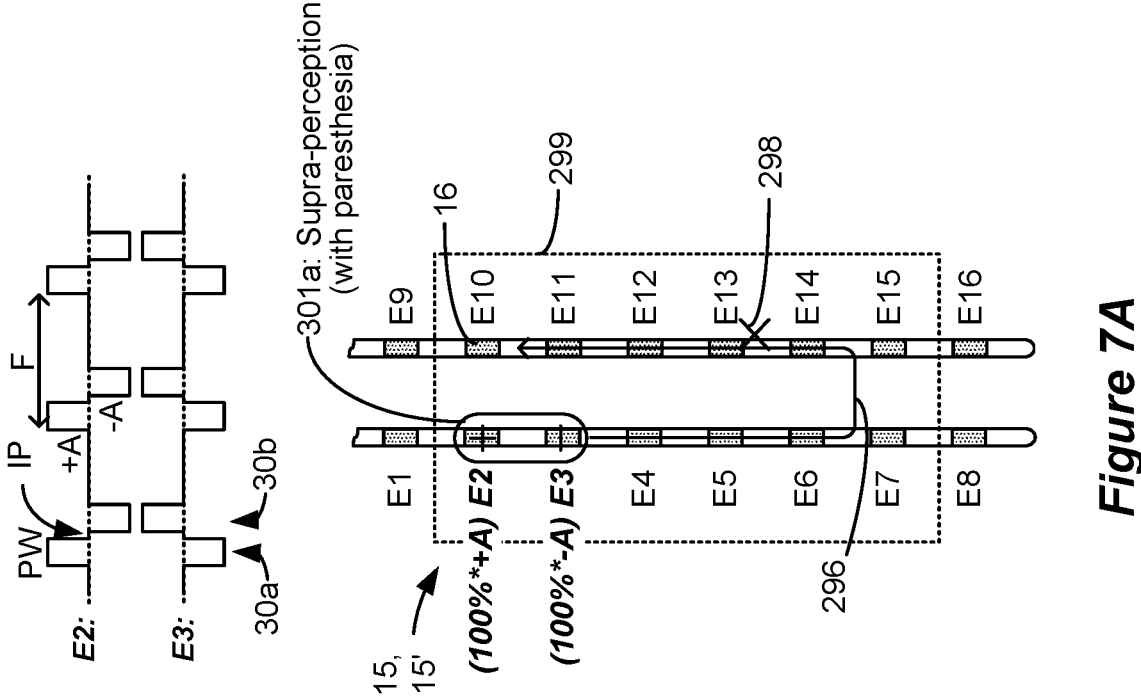
FIGS. 7A-7D show sweet spot searching to determine effective electrodes for a patient using a movable supra-perception bipole.

However, the inventors have determined that even if sub-perception therapy is eventually to be used for the patient, it can be beneficial to use supra-perception stimulation—that is, stimulation with accompanying paresthesia-during the sweet spot search. This is shown in FIG. 7A, where the movable bipole 301a provides supra-perception stimulation that can be felt by the patient. Providing bipole 301a as supra-perception stimulation can merely involve increasing its amplitude (e.g., current A) when compared to the sub-perception bipole 297a of FIG. 6, although other stimulation parameters might be adjusted as well, such as by providing longer pulse widths.

The inventors have determined that there are benefits to employing supra-perception stimulation during the sweet spot search even though sub-perception therapy will eventually be used for the patient.

First, as mentioned above, the use of supra-perception therapy by definition allows the patient to feel the stimulation, which enables the patient to provide essentially immediate feedback to the clinician whether the paresthesia seems to be well covering his pain site 298. In other words, it is not necessary to take the time to wash in bipole 301a at each location as it is moved along path 296. Thus, a suitable bipole 301a proximate to the patient's pain site 298 can be established much more quickly, such as within a single clinician's visit, rather than over a period of days or weeks.

In one example, when sub-perception therapy is preceded with supra-perception sweet spot searching, the time needed to wash in the sub-perception therapy can be one hour or less, ten minutes or less, or even a matter of seconds. This allows wash in to occur during a single programming session during which the patient's IPG or ETS is programmed, and without the need for the patient to leave the clinician's office.

Second, use of supra-perception stimulation during the sweet spot search ensures that electrodes are determined that well recruit the pain site 298. As a result, after the sweet spot search is complete and eventual sub-perception therapy is titrated for the patient, wash in of that sub-perception therapy may not take as long because the electrodes needed for good recruitment have already been confidently determined.

Figure 7B:
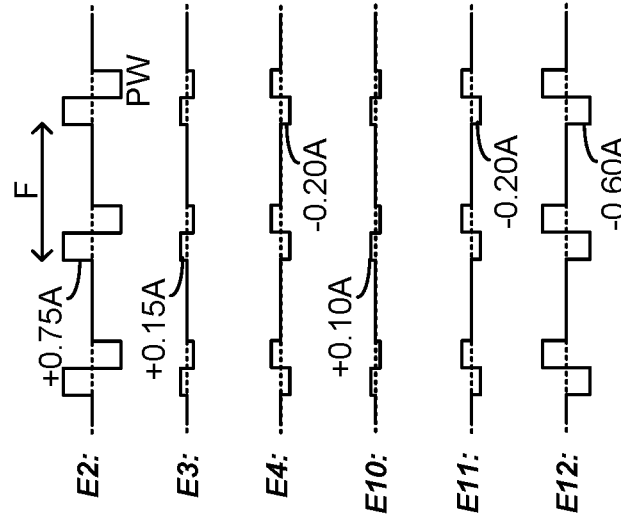
Figure 7B:
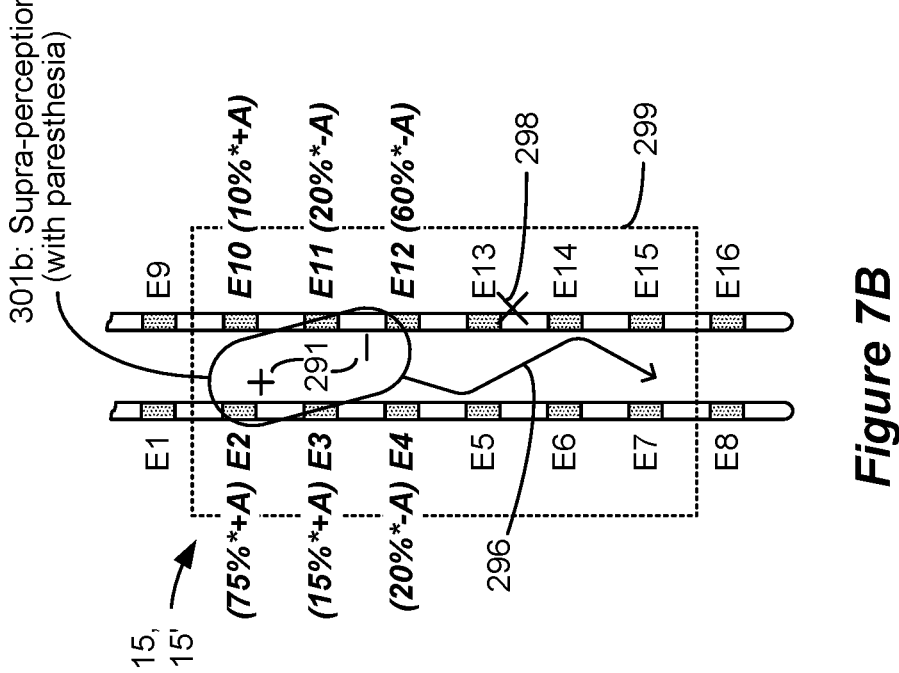
Figures 7C, 7D:
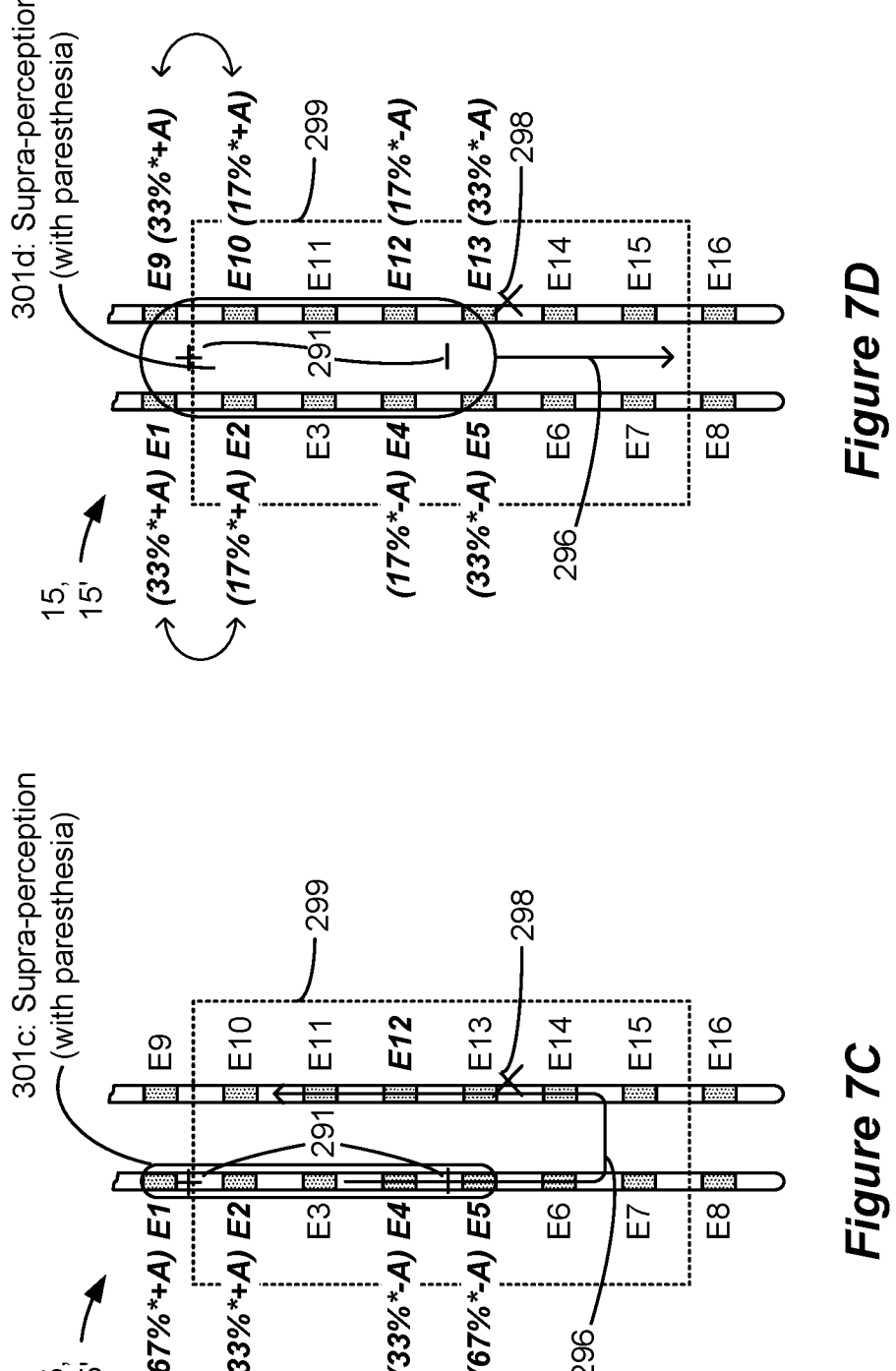

FIGS. 7B-7D show other supra-perception bipoles 301b-301d that may be used, and in particular show how the virtual bipoles may be formed using virtual poles by activating three or more of the electrodes 16. Virtual poles are discussed further in U.S. Pat. No. 10,881,859, which is incorporated herein by reference in its entirety, and thus virtual poles are only briefly explained here. Forming virtual poles is assisted if the stimulation circuitry 28 or 44 used in the IPG or ETS is capable of independently setting the current at any of the electrodes-what is sometimes known as a Multiple Independent Current Control (MICC), which is explained further below with reference to FIG. 8.

When a virtual bipole is used, the GUI 64 (FIG. 5) of the clinician programmer 50 (FIG. 4) can be used to define an anode pole (+) and a cathode pole (–) at positions 291 (FIG. 7B) that may not necessarily correspond to the position of the physical electrodes 16. The control circuitry 70 in the clinician programmer 50 can compute from these positions 291 and from other tissue modeling information which physical electrodes 16 will need to be selected and with what amplitudes to form the virtual anode and virtual cathode at the designated positions 291. As described earlier, amplitudes at selected electrodes may be expressed as a percentage X % of the total current amplitude A specified at the GUI 64 of the clinician programmer 50.

For example, in FIG. 7B, the virtual anode pole is located at a position 291 between electrodes E2, E3 and E10. The clinician programmer 50 may then calculate based on this position that each of these electrodes (during first pulse phase 30a) will receive an appropriate share (X %) of the total anodic current +A to locate the virtual anode at this position. Since the virtual anode's position is closest to electrode E2, this electrode E2 may receive the largest share of the specified anodic current +A (e.g., 75%*+A). Electrodes E3 and E10 which are proximate to the virtual anode pole's position but farther away receive lesser shares of the anodic current (e.g., 15%*+A and 10%*+A respectively). Likewise, it can be seen that from the designated position 291 of the virtual cathode pole, which is proximate to electrodes E4, E11, and E12, that these electrodes will receive an appropriate share of the specified cathodic current-A (e.g., 20%*–A, 20%*–A, and 60%*–A respectively, again during the first pulse phase 30a). These polarities would then be flipped during the second phases 30b of the pulses, as shown in the waveforms of FIG. 7B. In any event, the use of virtual poles in the formation of bipole 301b allows the field in the tissue to be shaped, and many different combinations of electrodes can be tried during the sweet spot search. In this regard, it is not strictly necessary that the (virtual) bipole be moved along an orderly path 296 with respect to the electrodes, and the path may be randomized, perhaps as guided by feedback from the patient.

FIG. 7C shows a useful virtual bipole 301c configuration that can be used during the sweet spot search. This virtual bipole 301c again defines a target anode and cathode whose positions do not correspond to the position of the physical electrodes. The virtual bipole 301c is formed along a lead-essentially spanning the length of four electrodes from E1 to E5. This creates a larger field in the tissue better able to recruit the patient's pain site 298. Note that in this bipole more than one electrode is active to form the anode (e.g., E1 and E2), and more than one anode is active to form the cathode (e.g., E4 and E5). With reference to the center of the bipole (e.g., E3), notice that anode electrodes farther from the center carry a larger percentage of the anodic current (e.g., with E1/E2 carrying 67%/33% respectively), and that that cathode electrodes farther from the center carry a larger percentage of the cathodic current (e.g., with E5/E4 carrying 67%/33% respectively). This could be varied: for example, E1 may carry 33%*+A, E2 67%*+A, E4 33%*–A, and E5 67%*–A. This bipole configuration 301c may need to be moved to a smaller number of locations than would a smaller bipole configuration compared 301a of FIG. 7A) as it moves along path 296, thus accelerating pain site 298 detection. FIG. 7D expands upon the bipole configuration of FIG. 7C to create a virtual bipole 301d using electrodes formed on both leads, e.g., from electrodes E1 to E5 and from electrodes E9 to E13. Again the fractionalization of the current can be varied, as shown using the arrows in FIG. 7D, where the amount of currents is flipped at E1 and E2, and at E9 and E10. This bipole 301d configuration need only be moved along a single linear path 296 along the electrode array that is parallel to the leads, as its field is large enough to recruit neural tissue proximate to both leads. This can further accelerate pain site detection.

In some aspects, the supra-perception bipoles 301a-301d used during the sweet spot search comprise symmetric biphasic waveforms having actively-driven (e.g., by the stimulation circuitry 28 or 44) pulse phases 30a and 30b of the same pulse width PW and the same amplitude (with the polarity flipped during the phases) (e.g., $A_{30a}=A_{30b}$, and $PW_{30a}=PW_{30b}$). This is beneficial because the second pulse phase 30b provides active charge recovery, with in this case the charge provided during the first pulse phase 30a ($Q_{30a}$) equaling the charge of the second pulse phase 30b ($Q_{30b}$), such that the pulses are charge balanced. Use of biphasic waveforms are also believed beneficial because, as is known, the cathode is largely involved in neural tissue recruitment. When a biphasic pulse is used, the positions of the (virtual) anode and cathode will flip during the pulse's two phases. This effectively doubles the neural tissue that is recruited for stimulation, and thus increases the possibility that the pain site 298 will be covered by a bipole at the correct location. In effect, the symmetric biphasic pulse provides two center points of stimulation to the tissue.

The supra-perception bipoles 301a-301d do not however need to comprise symmetric biphasic pulses as just described. For example, the amplitude and pulse width of the two phases 30a and 30b can be different, while keeping the charge (Q) of the two phases balanced (e.g., $Q_{30a}=A_{30a}*PW_{30a}=A_{30b}*PW_{30b}=Q_{30b}$). Alternatively, the two phases 30a and 30b may be charge imbalanced (e.g., $Q_{30a}=A_{30a}*PW_{30a}>A_{30b}*PW_{30b}=Q_{30b}$, or $Q_{30a}=A_{30a}*PW_{30a}<A_{30b}*PW_{30b}=Q_{30b}$). In short, the pulses in bipoles 301-301d can be biphasic symmetric (and thus inherently charge balanced), biphasic asymmetric but still charge balanced, or biphasic asymmetric and charge imbalanced.

In a preferred example, the frequency F of the supra-perception pulses 301a-301d used during the supra-perception sweet spot search may be 10 kHz or less, 1 kHz or less, 500 Hz or less, 300 Hz or less, 200 Hz or less, 130 Hz or less, or 100 Hz or less, or ranges bounded by two of these frequencies (e.g., 100-130 Hz, or 100-200 Hz). In particular examples, frequencies of 90 Hz, 40 Hz, or 10 Hz can be used, with pulses comprising biphasic pulses which are preferably symmetric. However, a single actively-driven pulse phase followed by a passive recovery phase could also be used. The pulse width PW may also comprise a value in the range of hundreds of microseconds, such as 150 to 400 microseconds. Because the goal of supra-perception sweet spot searching is merely to determine electrodes that appropriately cover a patient's pain, frequency and pulse width may be of less importance at this stage, or the frequency and pulse width used during the sweet spot searching can also be used for the eventual sub-perception. Once electrodes have been chosen for sub-perception stimulation, frequency and pulse width can be optimized, as discussed further below.

It is preferable that the same electrodes selected to position the supra-perception bipole 301a-d at an optimal location during the sweet spot are also selected during the sub-perception therapy that follows, although this isn't necessarily required. Instead, the best location of the bipole noticed during the search can be used as the basis to modify the selected electrodes. Suppose for example that a bipole 301a (FIG. 7A) is used during sweep spot searching, and it is determined that bipole provides the best pain relief when located at electrodes E13 and E14. At that point, sub-perception therapy using those electrodes E13 and E14 can be tried for the patient going forward. Alternatively, it may be sensible to modify the selected electrodes to see if the patient's symptoms can be further improved before sub-perception therapy is tried. For example, the distance (focus) between the cathode and anode can be varied, using virtual poles as already described. Or, a tripole (anode/cathode/anode) consisting of electrodes E12/E13/E14 or E13/E14/E15 could be tried, see U.S. Pat. No. 10,881,859 (discussing tripoles), and still other multipole configurations could be used as well. Or electrodes on a different lead could also be tried in combination with E13 and E14. For example, because electrodes E5 and E6 are generally proximate to electrodes E13 and E14, it may be useful to add E5 or E6 as sources of anodic or cathodic current (again creating virtual poles). All of these types of adjustments should be understood as comprising "steering" or an adjustment to the "location" at which therapy is applied, even if a central point of stimulation doesn't change (as can occur for example when the distance or focus between the cathode and anode is varied).

Figure 8:
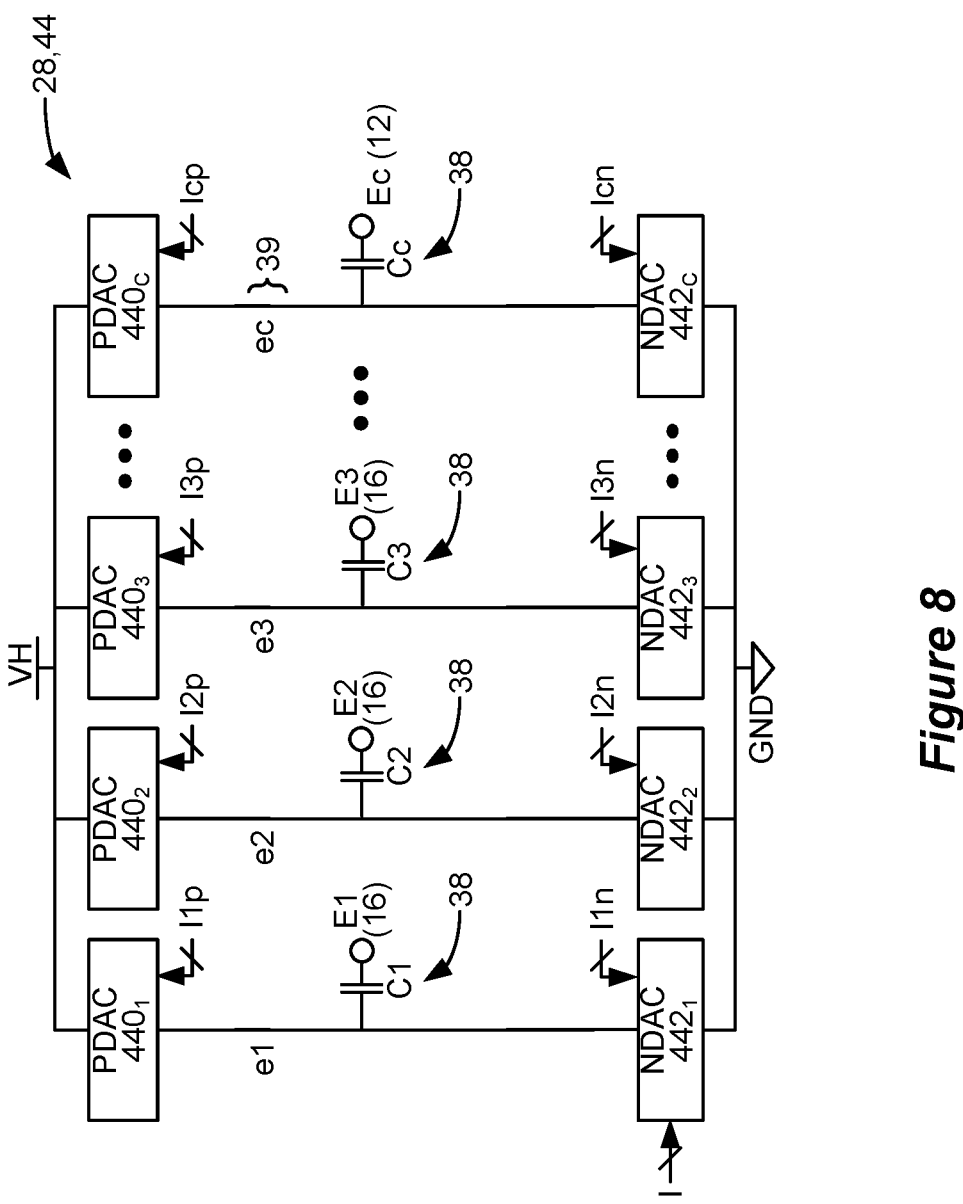
FIG. 8 shows stimulation circuitry useable in the IPG or ETS capable of providing Multiple Independent Current Control to independently set the current at each of the electrodes.

Multiple Independent Current Control (MICC) is explained in one example with reference to FIG. 8, which shows the stimulation circuitry 28 (FIG. 1) or 44 (FIG. 3) in the IPG or ETS used to form prescribed stimulation at a patient's tissue. The stimulation circuitry 28 or 44 can control the current or charge at each electrode independently, and using GUI 64 (FIG. 5) allows the current or charge to be steered to different electrodes, which is useful for example when moving the bipole 301i along path 296 during the sweet spot search (FIG. 7A-7D). The stimulation circuitry 28 or 44 includes one or more current sources 440i and one or more current sinks 442i. The sources and sinks 440i and 442i can comprise Digital-to-Analog converters (DACs), and may be referred to as PDACs 440i and NDACs 442i in accordance with the Positive (sourced, anodic) and Negative (sunk, cathodic) currents they respectively issue. In the example shown, a NDAC/PDAC 440i/442i pair is dedicated (hardwired) to a particular electrode node ei 39. Each electrode node ei 39 is preferably connected to an electrode Ei 16 via a DC-blocking capacitor Ci 38, which act as a safety measure to prevent DC current injection into the patient, as could occur for example if there is a circuit fault in the stimulation circuitry 28 or 44. PDACs 440i and NDACs 442i can also comprise voltage sources.

Proper control of the PDACs 440i and NDACs 442i via GUI 64 allows any of the electrodes 16 and the case electrode Ec 12 to act as anodes or cathodes to create a current through a patient's tissue. Such control preferably comes in the form of digital signals Iip and Iin that set the anodic and cathodic current at each electrode Ei. If for example it is desired to set electrode E1 as an anode with a current of +3 mA, and to set electrodes E2 and E3 as cathodes with a current of −1.5 mA each, control signal I1p would be set to the digital equivalent of 3 mA to cause PDAC 440₁ to produce+3 mA, and control signals I2n and I3n would be set to the digital equivalent of 1.5 mA to cause NDACs 442₂ and 442₃ to each produce-1.5 mA. Note that definition of these control signals can also occur using the programmed amplitude A and percentage X % set in the GUI 64. For example, A may be set to 3 mA, with E1 designated as an anode with X=100%, and with E2 and E3 designated at cathodes with X=50%. Alternatively, the control signals may not be set with a percentage, and instead the GUI 64 can simply prescribe the current that will appear at each electrode at any point in time.

In short, the GUI 64 may be used to independently set the current at each electrode, or to steer the current between different electrodes. This is particularly useful in forming virtual bipoles, which as explained earlier involve activation of more than two electrodes. MICC also allows more sophisticated electric fields to be formed in the patient's tissue.

Other stimulation circuitries 28 can also be used to implement MICC. In an example not shown, a switching matrix can intervene between the one or more PDACs 440i and the electrode nodes ei 39, and between the one or more NDACs 442i and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, and U.S. Patent Application Publications 2018/0071513, 2018/0071520, and 2019/0083796.

Much of the stimulation circuitry 28 or 44, including the PDACs 440i and NDACs 442i, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with the IPG's or ETS's telemetry antennas), circuitry for generating the compliance voltage VH that powers the stimulation circuitry, various measurement circuits, etc.

While it is preferred to use sweet spot searching, and in particular supra-perception sweet spot searching, to determine the electrodes to be used during subsequent sub-perception therapy, it should be noted that this is not strictly necessary. Sub-perception therapy can be preceded by subperception sweet spot searching, or may not be preceded by sweet spot searching at all. In short, sub-perception therapy may not be reliant on the use of any sweet spot search.

Figure 4:
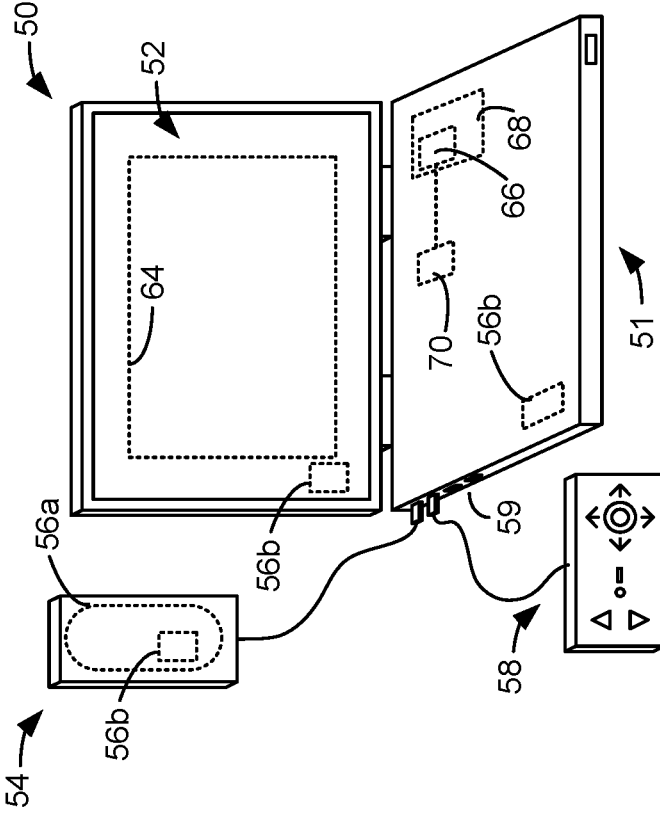
FIG. 4 shows various external devices capable of communicating with and programming stimulation in an IPG and ETS, in accordance with the prior art.
Figure 4:
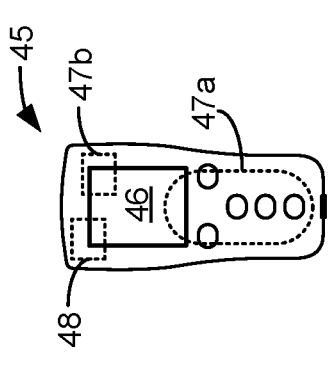
Figure 5:
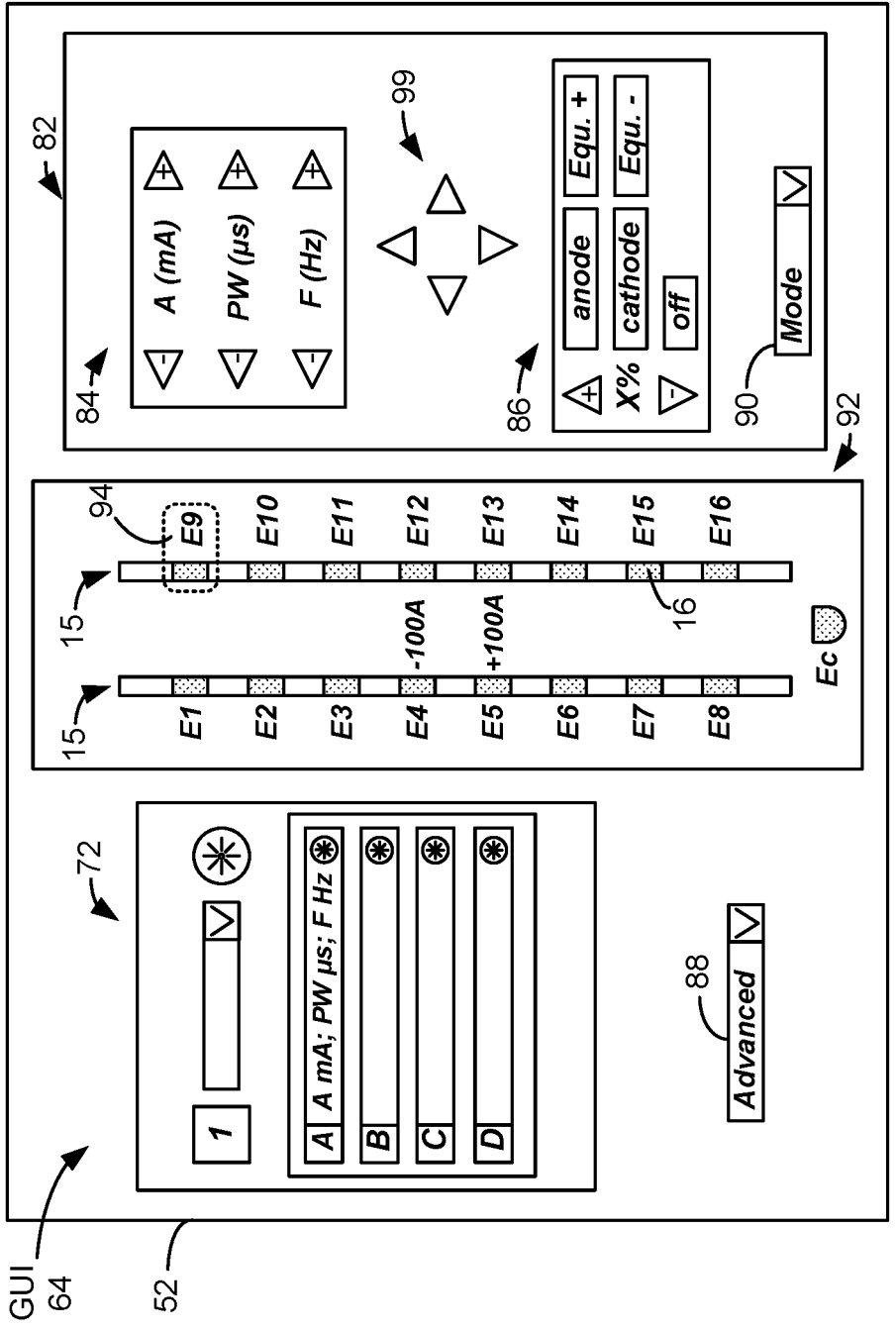
FIG. 5 shows a Graphical User Interface (GUI) of a clinician programmer external device for setting or adjusting stimulation parameters, in accordance with the prior art.
Figure 9:
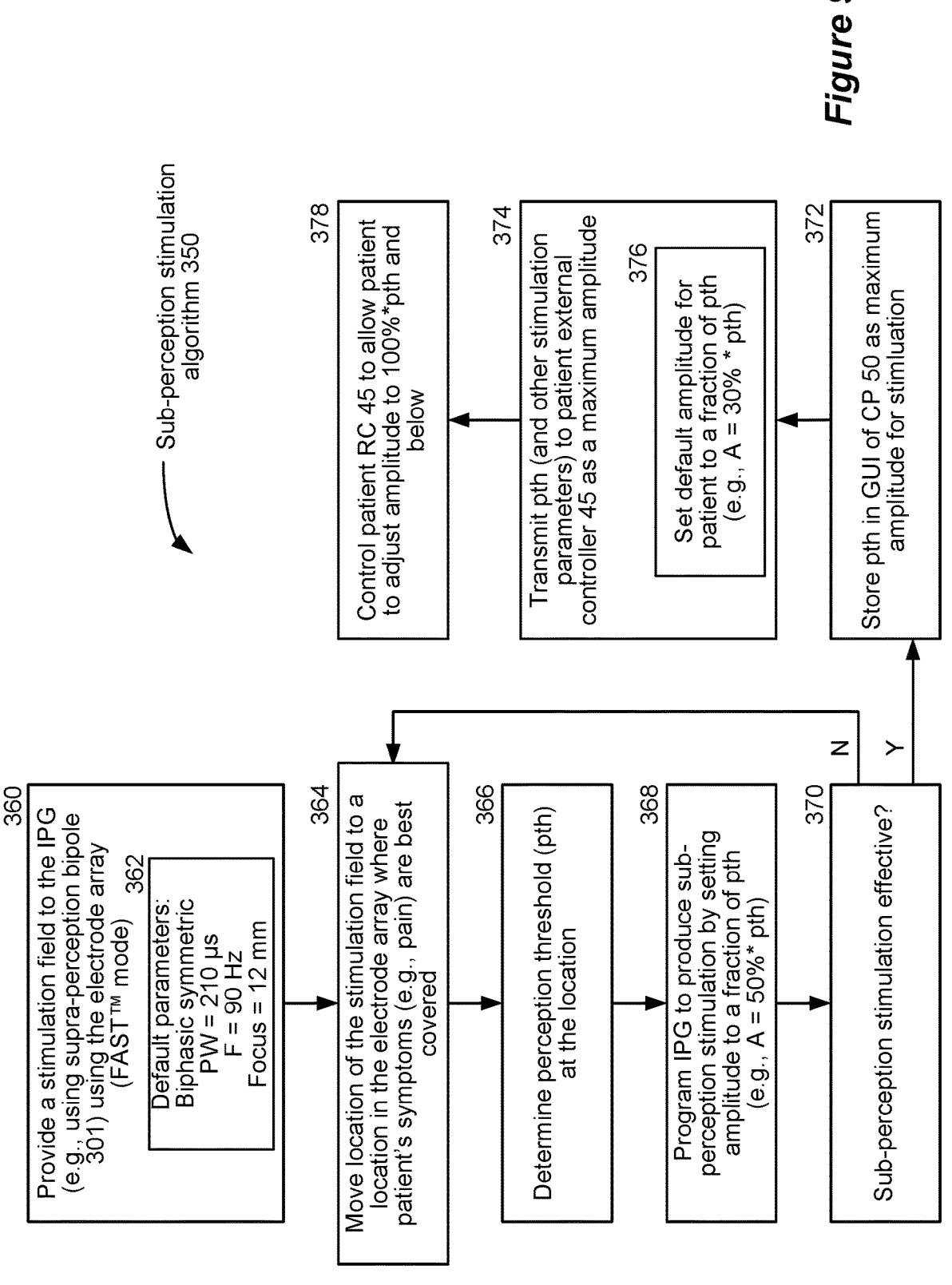
FIG. 9 shows a sub-perception stimulation algorithm used to optimize sub-perception stimulation for the patient.
Figure 10:
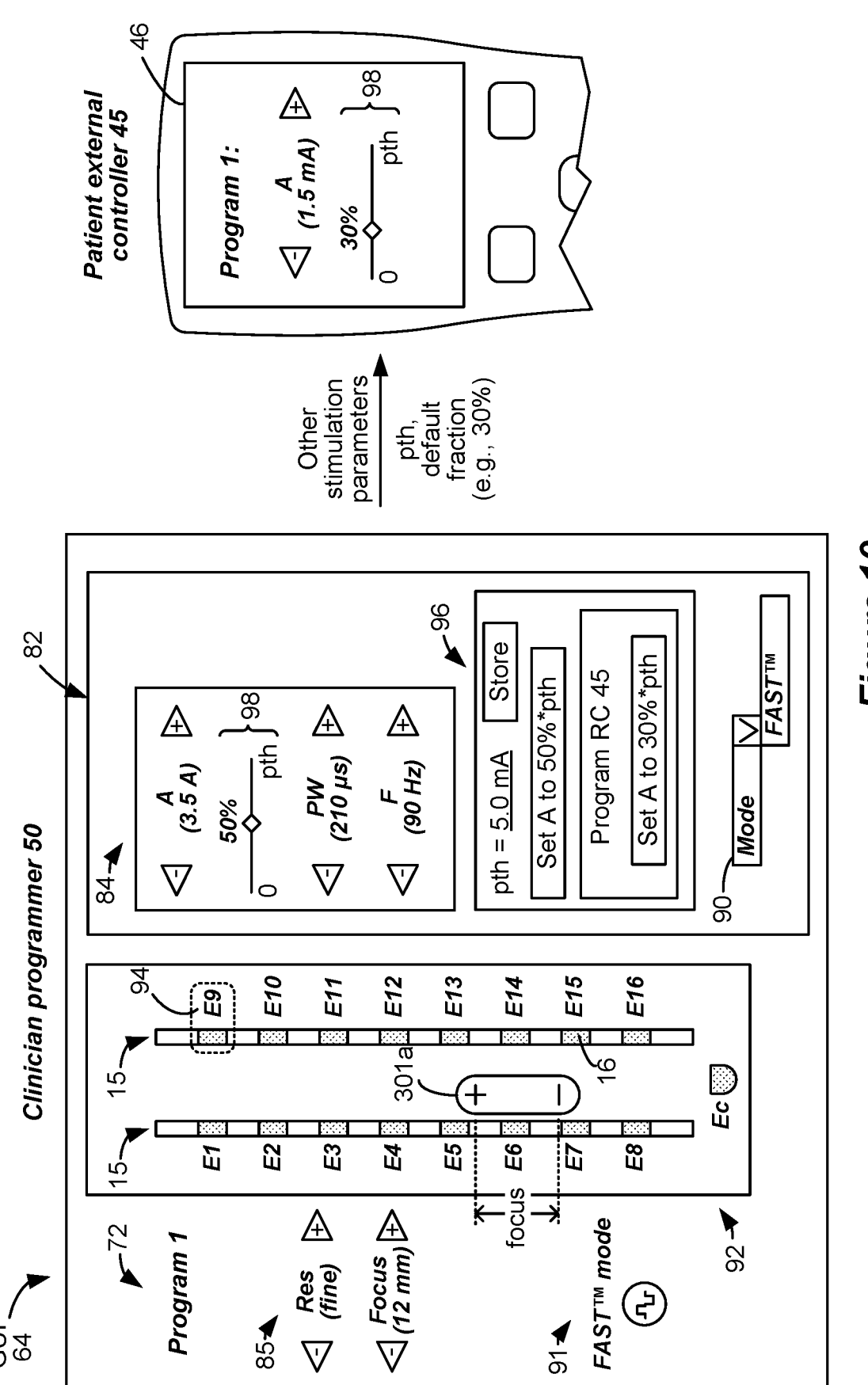
FIG. 10 shows aspects of the graphical user interfaces at both a clinician programmer and a patient remote control that are implicated during use of the sub-perception algorithm.

FIG. 9 discloses a sub-perception algorithm 350 that details steps that can be used to provide fast-acting sub-perception stimulation therapy for a patient. Some of the steps in algorithm 350 are automated in the clinician programmer (CP) 50 described earlier, although aspects of the algorithm can also be implemented in or affect the patient's external remote controller (RC) 45 (FIG. 4). FIG. 10 shows aspects of the GUI's of the CP 50 and RC 45 as implicated by the algorithm 350. Note that sub-perception algorithm 350 does not need to occur in the exact order shown. Further, steps can be removed from or added to the algorithm as depicted.

Steps 360-364 show steps implicated during the sweet spot search described above. In step 360, the CP 50's GUI 64 is used to provide a stimulation field to the patient. Preferably, and as discussed earlier (FIGS. 7A-7D), the stimulation field comprises supra-perception stimulation formed as bipole 301 (e.g., any of bipoles 301a-301d described earlier) in the electrode array, which can comprise leads 15 or 15' depending whether the implant the patient has received in an IPG 10 or ETS 40. Because the bipole 301 is supra-perception, note that the amplitude A for the bipole 301 at step 360 may be adjusted in the CP 50 to ensure that the stimulation can be comfortably felt by the patient as paresthesia. While use of a bipole 360 is preferred to provide the stimulation field, other pole configurations could be used as well. For example, a tripole could be used comprising two poles of a given polarity (e.g., anode poles) surrounding a third pole of the opposite polarity (a cathode pole). Still other multipole configurations could be used as well. For simplicity, the following example assume the use of a bipole for the pole configuration. Furthermore, while it is preferred that the stimulation field comprise supra-perception stimulation, this is not strictly required, and sub-perception stimulation could be used in other examples. Again, the following example assumes the use of supra-perception stimulation for simplicity.

Step 360 can be initiated using mode menu 90 in the GUI 64, as shown in FIG. 10, which essentially allows steps in the sub-perception algorithm 350 to run. As shown in FIG. 10, the relevant mode is called FAST™, because it allows sub-perception stimulation to be established quickly for the patient. An indicator 91 can be provided in the GUI 64 to make clear to the clinician that this mode has been selected. Certain default stimulation parameters for the bipole 301 can be used which have been noticed to be effective, as shown in step 362, and these default parameters can either be manually entered in the GUI 64 or automatically populated upon selection of the FAST mode. For example, the stimulation field (e.g., supra-perception bipole 301) can be formed using actively-driven symmetric biphasic waveforms. As discussed earlier, symmetric biphasic waveforms are beneficial because they promote active charge recovery at the relevant electrodes, and because the flipping of the polarity at those electrodes (from phase 30a to 30b) effectively doubles the neural tissue that is recruited for stimulation to increases the possibility that the pain site 298 will be covered by the bipole when it is set at the correct location. However, active charge recovery, while preferred, is not strictly required, and the stimulation field can be provided using other types of waveforms.

Step 362 also sets other default parameters for the supra-perception bipole 301, such as its pulse width PW=210 microseconds (of pulse phase 30a), the frequency of the pulses F=90 Hz. Generally speaking, the frequency may be 130 Hz or less, and the pulse width may range from 160 to 260 microseconds. A default focus (distance) between the poles (e.g., 12 mm) may also be set, as shown at GUI element 85. Still further, a default resolution (e.g., fine) may also be used, as also shown at GUI element 85. A fine resolution allows the bipole to be moved in the electrode array at fine increments (e.g., 0.1 mm), which is useful in subsequent steps. Although not shown, the position of the bipole 301 in the electrode array can also be set as a default starting point, or a present or previously-determined location of the bipole can be used as well. While these parameters may be used as defaults, they may also be made adjustable in the CP, as shown in FIG. 10.

At step 364, and using the CP 50, the stimulation field (e.g., supra-perception bipole 301) is moved in the electrode array to a location that best covers the patient's symptoms, such as pain. As discussed earlier, such sweet spot searching seeks to position the bipole 301 proximate to a pain site 298. In this step 364, the optimal goal is to have the patient feel only the paresthesia of the stimulation field (assuming it is supra-perception) and little or no pain. As discussed above, the use of supra-perception stimulation enables the patient to provide essentially immediate feedback to the clinician regarding pain coverage. Pain coverage at step 364 may be assessed using patient pain scores as described earlier or other rating scales. If the stimulation field provides sub-perception stimulation, the goal is to have the patient feel little or no pain. As described earlier, the position of the bipole 301 can be moved in the electrode array in small increments (preferably with a fine resolution), and may be established as virtual poles as it is moved along a path 296. Although not shown in FIG. 10 for simplicity, directional arrows 99 (FIG. 5) or other peripheral devices connected to the CP 50, can be used to move the bipole 301.

When moving the stimulation field (e.g., supra-perception bipole 301) to new locations during step 364, it may be beneficial to wait for a wash out period before stimulation is provided at a new location. A "wash out" period comprises a period of time after the cessation of stimulation therapy during which the benefits of stimulation therapy (e.g., pain reduction) are still present. Typically when a supra-perception bipole 301 is used, such wash out may be a number of minutes, and therefore it may be preferred to wait this duration of time after providing stimulation at a first location before providing stimulation at a next location. This is preferred to ensure that previous stimulation does not affect results when assessing coverage and effectiveness at a new location. Note that a wash out period may need to be longer if the preceding stimulation had been established for a longer period of time. Sub-perception stimulation if used for bipole 301 may also require waiting for longer wash out periods as well.

Furthermore, it may be necessary to adjust the supra-perception amplitude of the stimulation field each time it is moved, so that the patient generally feels a constant level of paresthesia (e.g., a low-to-medium sense of paresthesia). In this regard, note that different electrodes in the array may be closer to or farther from the spinal cord. Thus as the stimulation field is moved to new electrodes, the stimulation may be more strongly felt or less strongly felt by the patient, meaning that the amplitude should be adjusted down or up to compensate and to achieve a generally uniform intensity of paresthesia at all tested locations. Failing to normalize the intensity of perceived paresthesia may confuse the patient's ability to assess pain coverage (e.g., by assuming very intense stimulation well covers pain when in fact it does not).

It may also be useful to test each location- and in particular the last "best" location—at a very low level of paresthesia to ensure or double check pain coverage. If pain overlap is not 100%, other stimulation parameters of the stimulation field such as focus and pulse width can be adjusted to see if even better coverage can be achieved.

It may be useful once the best location is found to test other locations very close to this location to see if the best location can be finely tuned. For example, if a number of very close locations are tested, all showing the good (or best) results, the best location may be determined to be at the center of those locations. This is preferred to ensure that therapy will still be effective to treat the patient's symptoms even if the electrodes move or migrate slightly in the patient's spinal column.

It may also be useful to have the patient use the resulting simulation field at the best location for a short period of time to verify effective of therapy. Effectiveness can be determined using patient feedback, which again can occur by having the patient score or rank their symptoms. Although not shown, the clinician may have the patient engage in certain activities (e.g., walking), or to position themselves in different postures (e.g., sitting, standing, etc.) to ensure that therapy is effective at the best location. In a sense, the clinician may have the patient give the stimulation field a "test drive" at step 364 before proceeding to next steps.

At step 366, a perception threshold pth is determined for the stimulation field (e.g., bipole 301) provided at the location determined in step 364. Perception threshold pth can be expressed using a stimulation parameter such as amplitude A, and generally denotes a threshold between sub-perception stimulation and supra-perception stimulation. As such, pth can comprise a maximum amplitude at which the patient cannot feel the stimulation, and/or as a minimum amplitude at which the patient can still feel the stimulation. Determining pth can be assisted using the GUI 64 of the CP 50 as shown in FIG. 10, and in particular can be determined by adjusting the amplitude A of the bipole 301 up or down in waveform parameter interface 84. For example, the amplitude A can be gradually increased the amplitude A to a point where the patient reports feeling the stimulation (paresthesia), or the amplitude can be gradually decreased to a point where the patient reports no longer feels the stimulation. Once determined, the perception threshold pth can be marked or otherwise entered into the GUI 64 of the CP. This can occur in different ways, but in the example of FIG. 10, the determined pth can be typed into a field in a perception threshold interface 96. The perception threshold pth can also be stored in the CP 50, although it may also be useful to do this later after verifying that sub-perception stimulation works well for the patient, as discussed in next steps 368 and 370. In the example of FIG. 10, it is assumed that pth=5 mA.

At step 368, the stimulation field (e.g., bipole 301) at the location is adjusted to a sub-perception level by adjusting the amplitude to a fraction of pth. This can involve the clinician adjusting the amplitude to a value below pth, for example using waveform parameter interface 84. Alternatively, the GUI 64 may include a selectable option to apply a default fraction to pth, such as 50%, as shown in perception threshold interface 96. Still alternatively, once pth has been entered and stored, a different means for adjusting the amplitude may be provided in the GUI 64. For example, and as shown in FIG. 10, the waveform parameters interface 84 can include an adjustment mechanism such as a slider 98 to allow the amplitude to be adjusted to sub-perception levels between 0 mA (or some other minimum value) and 100%*pth. Regardless of how this occurs, application of the 50% faction sets the amplitude to 2.5 mA (e.g., 50%*5 mA), and the IPG is programmed accordingly.

At step 370, the effectiveness of providing sub-perception stimulation with the bipole 301 at the location is verified. As discussed above, having initially used a fast-acting supra-perception bipole 301 during sweet spot searching to determine an optimal stimulation location (364), it is expected that the sub-perception stimulation provided at step 368 will wash in quickly. Effectiveness can be determined at step 370 using patient feedback, which again can occur by having the patient score or rank their symptoms. Although not shown, the clinician at step 370 may have the patient engage in certain activities (e.g., walking), or to position themselves in different postures (e.g., sitting, standing, etc.) to ensure that the sub-perception therapy is effective in reducing symptoms under a variety of conditions. If the efficacy of the sub-perception stimulation is not optimal at step 370, the sub-perception algorithm 350 can return to earlier steps to try to improve the situation. For example, as shown in FIG. 9, the algorithm 350 can return to step 364 to repeat the supra-perception sweet spot search in the hopes of finding a better location for the bipole in the electrode array 301 that better covers the patient's symptoms.

Once suitable sub-perception therapy has been verified (step 370), the now-vetted perception threshold pth can be stored in the CP 50 (step 372) as a maximum amplitude, as shown in perception threshold interface 96. This may have also occurred earlier in the process, such as at step 366 when the perception threshold was first entered in the GUI 64. Although not shown, note that pth may be stored with information regarding the location of the bipole, as defined by the active electrodes, their polarities, and their currents, as described above. This is beneficial because pth may change depending on where in the electrode array the bipole 301 is positioned, and in this regard, the CP 50 may store numerous pth values each associated with different bipole positions. Note that pth may also be stored with the stimulation program (Program 1) used to form the bipole 301, and as such may be stored with all relevant stimulation parameters (such as A, F, PW, etc.).

Once pth has been verified as effective and stored in the CP 50, the algorithm 350 can undertake steps to allow the patient to control the sub-perception therapy, which can be affected by programming the patient RC 45 at step 374. Programming the patient's RC 45 can occur in different ways, but in FIG. 10, a selectable option is provided in the perception threshold interface 96. This input may also allow the clinician to set a default fraction of pth as the amplitude for the patient (step 376). This default fraction may be different from the fraction of pth that was used earlier to verify the efficacy of sub-perception stimulation (at steps 368, 370). For example, in the depicted example, the default fraction is set to 30%*pth, although this may also be adjustable by the clinician using the GUI 64. Setting the default fraction to be relatively low may be preferable, because it will allow the patient RC 45 to both increase and decrease the amplitude throughout a sub-perception range of amplitudes, as explain subsequently.

Upon selection of the programming option, the CP 50 can transmit the pth, the default fraction (30%), as well as other stimulation parameters to the patient's RC 45. Preferably the stimulation parameters include those necessary to form the bipole at the determined location (364), and so such stimulation parameters will include an indication of which electrodes are active, and with what polarities and relative strengths, as discussed above. The stimulation parameters will also include information necessary to form the stimulation as symmetric biphasic waveforms with the proper frequency (F) and pulse width (PW), which may be those used earlier as defaults (362). In effect, the CP 50 transmits a stimulation program to the RC 45, including pth variables that will be used to limit the amplitude to sub-perception levels at the RC 45, as explained next.

At step 378, the now-programmed RC 45 can be used by the patient to control the IPG to produce the stimulation program defining the symmetric biphasic bipole. In one example, the patient may only be able to adjust the amplitude of the stimulation, as explained further below. However, in other examples, other stimulation parameters, such as pulse width (PW) and frequency (F) may be adjustable by the patient using the RC 45, although perhaps only slight adjustments from default values may be allowed. Experience teaches that an effective amplitude for typical activities will be about 40% to 60% of pth. Because sub-perception therapy achieved using algorithm 350 has been noted to have a possible curative effect, it is possible that a patient may be able to gradually reduce the amplitude of the sub-perception stimulation over time. Also, if a patient experiences side effects such as headache, cramps, pressure, heavy limbs, or general discomfort, the patient should be advised to decrease the sub-perception amplitude even if pain symptoms are under control. On the other hand, if a patient starts to experiencing pain symptoms, the patient should be advised to increase the sub-perception amplitude to bring their pain symptoms back under control.

Although not shown, the patient may also provide sub-perception therapy at step 378 in boluses—e.g., by providing sub-perception stimulation at 80%*pth for 30-60 minutes every 2-4 hours. Preferably, a patient would not exceed use of six bolus of stimulation in a 24 hours period. Providing boluses of stimulation is described further in PCT (Int'l) Patent Application Publication 2021/178105which is incorporated herein by reference in its entirety.

FIG. 10 shows the graphical user interface of the RC 45 once it has been programmed as just described. Significantly, the previously-determined perception threshold pth preferably comprises a maximum amplitude that the patient can select (100%*pth), and so limits control to only sub-perception amplitudes. In FIG. 10, the default fraction of 30% has been applied, and thus an amplitude of 30%*pth (e.g., 1.5 mA) is being produced, although the patient can increase or decrease this amplitude using the GUI of the RC 45. In this regard, the patient RC 45 may include user interface elements similar to those described earlier for the CP 50. For example, the GUI include a slider 98 which limits the amplitude A to from 0 mA (or some minimum value) to 100%*pth. In one example, the RC 45 may not display an actual current amplitude (in mA), as this value may be too technical and not understandable to the patient. Instead, the RC 45 may only display a relative sub-perception amplitude from 0 to 100%, which may be more intuitive for the patient. Still other amplitude indicators (e.g., a number of bars, or various other numbers) can be used to indicate sub-perception amplitude as well.

Various aspects of the disclosed techniques, including processes implementable in the IPG or ETS, or in external devices such as the clinician programmer or patient external controller to render and operate the GUI, can be formulated and stored as instructions in a computer-readable media associated with such devices, such as in a magnetic, optical, or solid state memory. The computer-readable media with such stored instructions may also comprise a device readable by the clinician programmer or external controller, such as in a memory stick or a removable disk, and may reside elsewhere. For example, the computer-readable media may be associated with a server or any other computer device, thus allowing instructions to be downloaded to the clinician programmer system or external controller or to the IPG or ETS, via the Internet for example.

The disclosed techniques for providing sub-perception stimulation to the patient, and sub-perception threshold algorithm 350, can be modified in many different ways, some of which are disclosed in the above-incorporated '867 Application. For example, and as disclosed in the '867 Application, the pulse width and frequency used for either the supra-perception bipole or the subsequent sub-perception stimulation can be selected using information relating pulse widths and frequencies. The amplitude may also be optimized for sub-perception stimulation, which can involve determine the perception threshold at different pulse widths. Subsets of optimal sub-perception stimulation parameters, each defining a stimulation mode, can be selected, where at least some of the stimulation modes are optimized for use assuming various circumstances of the patient (e.g., sleeping, exercising, etc.). Such circumstances can also be automatically detected, and thus the correct stimulation mode and corresponding subset of parameters applied. The sub-perception stimulation can be prescribed using a neural dose, expressible for example as a mean charge per-second. Further, sub-perceptions stimulation can be modulated in different manners to change the charge-per-second delivered to the patient as a function of time. The sub-perception stimulation can be automatically varied with determined optimal stimulation parameters to prevent tissue habituation. The patient RC can be programmed to allow the patient to move the sub-perception stimulation in the electrode array within a prescribed range. A fitting algorithm can be used to assist in selecting optimal sub-perception stimulation parameters, which may receive one or more of pain information, mapping information, spatial field information, and phenotype information as inputs. Again, these concepts are discussed in further details in the above-incorporated '867 Application, which with the reader is assumed familiar.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for programming a stimulator having a plurality of electrodes comprising an array, the method comprising:

(a) using a first external device to provide a stimulation field to the stimulator, wherein the stimulation field comprises a pole configuration formed in the electrode array;

(b) using the first external device to move the pole configuration in the electrode array to a location that best treats a symptom of the patient;

(c) determining using the first external device a perception threshold of the pole configuration at the location by varying an amplitude of the stimulation field;

21

(d) adjusting the amplitude using the first external device to below the perception threshold to produce sub-perception stimulation at the location; and (e) using the first external device to program a second external device usable by the patient with the determined perception threshold, wherein the second external device is useable by the patient to adjust an amplitude of the sub-perception stimulation, wherein the perception threshold limits adjustment of the amplitude by the patient.

2. The method of claim 1, wherein the first external device programs the second external device to a default amplitude of less than the determined perception threshold.

3. The method of claim 1, wherein the stimulator comprises a spinal cord stimulator.

4. The method of claim 1, wherein the stimulation field provides supra-perception stimulation.

5. The method of claim 1, wherein the pole configuration comprises a bipole comprising an anode pole and a cathode pole.

6. The method of claim 5, wherein when the bipole is at the location, the anode pole is formed at two or more electrodes, and wherein the cathode pole is formed at two or more different of the electrodes.

7. The method of claim 5, wherein the bipole comprises an anode pole and a cathode pole, wherein more than one electrode is active to form the anode pole, and wherein more than one electrode is active to form the cathode pole.

8. The method of claim 1, wherein the first external device is used to move the pole configuration linearly along a length of the electrode array.

9. The method of claim 1, wherein the pole configuration comprises actively-driven symmetric biphasic pulses at active ones of the electrodes.

10. The method of claim 1, wherein the pulses are formed at a frequency of 130 Hz or less.

11. The method of claim 1, wherein the pulses have a pulse width within a range from 50 to 500 microseconds.

12. The method of claim 11, wherein the pulses have a pulse width within a range from 160 to 260 microseconds.

13. The method of claim 1, wherein the method is initiated at the external device by receiving a mode selection at an interface of the external device.

14. The method of claim 1, wherein in step (d) the amplitude is adjusted to a programmed fraction of the perception threshold.

15. The method of claim 1, wherein in step (e) the amplitude adjustment at the second external device cannot exceed the perception threshold.

16. A first external device to program a stimulator having a plurality of electrodes comprising an array, comprising:

control circuitry configured to render a user interface, wherein the user interface enables a user to (a) provide a stimulation field to the stimulator, wherein the stimulation field comprises a pole configuration formed in the electrode array;

(b) move the pole configuration in the electrode array to a location that best treats a symptom of the patient;

(c) determine a perception threshold of the pole configuration at the location by varying an amplitude of the stimulation field;

(d) adjust the amplitude to below the perception threshold to produce sub-perception stimulation at the location; and (e) program a second external device usable by the patient with the determined perception threshold, wherein the second external device is useable by the patient to adjust an amplitude of the sub-perception stimulation, wherein the perception threshold limits adjustment of the amplitude by the patient.

17. The first external device of claim 16, wherein the stimulation field provides supra-perception stimulation.

18. A non-transitory computer readable medium containing instructions executable on a first external device configured to program a stimulator having a plurality of electrodes comprising an array, wherein the instruction when executed enable a user to:

(a) provide a stimulation field to the stimulator, wherein the stimulation field comprises a pole configuration formed in the electrode array;

(b) move the pole configuration in the electrode array to a location that best treats a symptom of the patient;

(c) determine a perception threshold of the pole configuration at the location by varying an amplitude of the stimulation field;

(d) adjust the amplitude to below the perception threshold to produce sub-perception stimulation at the location; and (e) program a second external device usable by the patient with the determined perception threshold, wherein the second external device is useable by the patient to adjust an amplitude of the sub-perception stimulation, wherein the perception threshold limits adjustment of the amplitude by the patient.

* * * * *